United States Patent [19]

Weis

[11] 4,284,828
[45] Aug. 18, 1981

[54] PROCESS FOR THE MANUFACTURE OF 4,5-DICHLORO-2-(4-CHLOROPHENOXY)-PHENOL

[75] Inventor: Claus D. Weis, Pfeffingen, Switzerland

[73] Assignee: Ciba-Geigy Corporation, Ardsley, N.Y.

[21] Appl. No.: 92,814

[22] Filed: Nov. 9, 1979

[30] Foreign Application Priority Data

Nov. 21, 1978 [CH] Switzerland ............... 11919/78

[51] Int. Cl.³ ............................................. C07C 41/22
[52] U.S. Cl. ................................................... 568/637
[58] Field of Search ........................................ 568/637

[56] References Cited

U.S. PATENT DOCUMENTS 3,506,720  4/1970  Model et al. ............... 568/637
3,904,696  9/1975  Model et al. ............... 568/637

Primary Examiner—Bernard Helfin
Attorney, Agent, or Firm—Edward McC. Roberts; John P. Spitals

[57] ABSTRACT

A process for the manufacture of 4,5-dichloro-2-(4-chlorophenoxy)phenol by selective chlorination of 2-phenoxyanisole with 3 to 5 molar equivalents of chlorine, in the temperature range between $-10°$ and $+50°$ C., preferably between $0°$ and $30°$ C., in a lower halogenated aliphatic hydrocarbon, a lower aliphatic nitrile, in dimethyl formamide, dimethylmethanephosphonate or methanol, preferably in dimethyl formamide, dimethylmethanephosphonate, methanol, acetonitrile, propionitrile, chloroform, methylene chloride, 1,2-dichloroethane or tetrachloroethane, and demethylation of the 4,5-dichloro-2-(4-chlorophenoxy)anisole obtained as intermediate with an acid.

10 Claims, No Drawings

PROCESS FOR THE MANUFACTURE OF 4,5-DICHLORO-2-(4-CHLOROPHENOXY)-PHENOL

The present invention relates to a process for the manufacture of 4,5-dichloro-2-(4-chlorophenoxy)-phenol and to a process for the manufacture of 4,5-dichloro-2-(4-chlorophenoxy)anisole obtained as intermediate.

4,5-Dichloro-2-(4-chlorophenoxy)phenol (=4,4′,5-trichloro-2-hydroxydiphenyl ether) is known to be a compound having good antimicrobial action, as are also a number of further halogenated 2-hydroxydiphenyl ethers. Reference is made in this connection to the following publications: U.S. Pat. Nos. 3,904,696, 3,629,477 and 3,800,048 and Swiss patent specification 432 119. These publications also describe different methods of obtaining these 2-hydroxydiphenyl ethers, namely: (a) Reduction of the nitro group of a halogeneted o-nitrodiphenyl ether to the amino group, diazotisation of this latter and substitution of the diazonium group by the hydroxyl group. The halogenated o-nitrodiphenyl ether required as starting material can be obtained by condensation of a corresponding 1-nitro-2-halobenzene with an unsubstituted or halogen-substituted phenol. (b) Condensation of a 1-nitro-2- (or -4-)halobenzene with an unsubstituted or halogen-substituted 1-hydroxy-2-alkoxybenzene to produce an o- (or p-)nitro-o-alkoxydiphenyl ether, dealkylation of the alkoxy group, reduction of the nitro group to the amino group, diazotisation of this latter and substitution of the diazonium group by a halogen atom by the method of Sandmeyer, wherein the dealkylation can also be carried out as final step. (c) Condensation of a 1-alkoxy-2-chloro(or -bromo)benzene which may or may not contain further halogen atoms with an unsubstituted or halogenated phenolate in the presence of copper or copper(I) salts, and dealkylation of the resultant o-alkoxydiphenyl ether. (d) Halogenation of o-hydroxydiphenyl ethers, wherein a halogen atom is introduced into a o-hydroxydiphenyl ether which may or may not already be halogenated.

The above described methods (a) and (b) are relatively complicated, time-consuming and expensive, as they proceed via many steps and involve technically complicated operations (hydrogenation, diazotisation). In addition, they yield product mixtures having a high content of impurities and the separation and purification of which require laborious operations. Process (c) is carried out in the melt and the yields are only modest. In method (d) it is virtually only possible to halogenate already halogenated o-hydroxydiphenyl ethers, as otherwise usually mixtures of products are obtained.

U.S. Pat. No. 3,904,696 specifically describes the chlorination of a number of 2-phenoxyphenols containing at least 2 halogen atoms with sulfuryl chloride in chlorobenzene to produce the corresponding compounds which are substituted in the 5-position of the phenol ring, as well as the chlorination of 2-(4-chlorophenoxy)phenol with chlorine in glacial acetic acid to produce 3,5-dichloro-2-(4-chlorophenoxy)phenol, and also the analogous chlorination to produce a number of further 2-phenoxyphenols which are substituted in the 3- and 5-positions.

Finally, Belgian patent specification 659 636 describes the manufacture of 5-chloro-2-phenoxyphenol by chlorination of 2-phenoxyphenol with sulfuryl chloride and of 5-chloro-2-(4-chlorophenoxy)phenol by chlorination of 2-phenoxyanisole with chlorine in glacial acetic acid and subsequent demethylation.

Surprisingly, it has now been found that 4,5-dichloro-2-(4-chlorophenoxy)phenol can be obtained by selective chlorination of 2-phenoxyanisole in specific solvents and by demethylation of the 4,5-dichloro-2-(4-chlorophenoxy)anisole obtained as intermediate. This novel process avoids the above described disadvantages of the previously known methods for obtaining this compound. In addition, the compound is obtained in pure white crystalline form and has no unpleasant odour, as it does when it is obtained from the amine via diazotisation. It is especially surprising that the chlorination in one step yields the 4,5,4′-trichloro-o-methoxydiphenyl ether selectively and in high yield.

The process of the present invention for the manufacture of 4,5-dichloro-2-(4-chlorophenoxy)phenol of the formula

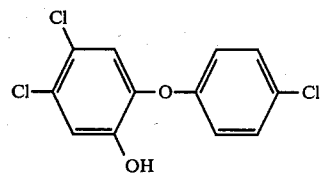

comprises selectively chlorinating one molar equivalent of 2-phenoxyanisole at a temperature between −10° and +50° C., in a lower halogenated aliphatic hydrocarbon which contains at least one hydrogen atom, a lower aliphatic nitrile, in dimethyl formamide, dimethylmethanephosphonate or methanol, with about 3 to 5 molar equivalents of chlorine, and demethylating the 4,5-dichloro-2-(4-chlorophenoxy) anisole obtained as intermediate with an acid.

The invention also relates to the manufacture of the 4,5-dichloro-2-(4-chlorophenoxy)anisole obtained as intermediate after the first step of the above process.

Lower halogenated aliphatic hydrocarbons which contain at least one hydrogen atom are preferably chlorinated alkanes or alkenes containing 1 to 6, in particular 1 to 4, carbon atoms, preferably chloroform, methylene chloride, 1,2-dichloroethane and tetrachloroethane.

Lower aliphatic nitriles contain preferably 2 to 5 carbon atoms and are in particular acetonitrile and propionitrile.

The chlorination is advantageously carried out in a chlorinated hydrocarbon containing 1 to 4 carbon atoms, an aliphatic nitrile containing 2 to 5 carbon atoms, in dimethyl formamide, dimethylmethanephosphonate or methanol.

Preferred solvents are dimethyl formamide, dimethylmethanephosphonate, methanol, acetonitrile, propionitrile, chloroform, methylene chloride, 1,2-dichloroethane and tetrachloroethane, in particular dimethyl formamide, acetonitrile, methylene chloride and 1,2-dichloroethane.

It is particularly advantageous to carry out the process in a halogenated alkane, such as chloroform or tetrachloroethane, but most preferably methylene chloride and 1,2-dichloroethane.

Depending on the solvent employed, the temperature during the chlorination can be between −10° and +50° C. At higher temperatures, higher chlorinated products are formed to an increasing degree. In general, the process is carried out in the temperature range between 0° and 30° C., preferably at room temperature.

In the chlorination, about 3 to 5 molar equivalents of chlorine are employed per molar equivalent of 2-phenoxyanisole. Larger amounts of chlorine promote the formation of higher chlorinated by-products, whilst smaller amounts diminish the yield. It is preferred to employ an amount of about 4 molar equivalents of chlorine per molar equivalent of 2-phenoxyanisole.

Before the chlorination it is possible to add catalytic amounts of different substances, whereupon often a slight increase in the yield is observed. Examples of such substances are iodine, triethylamine, and different salts, e.g. $FeCl_3$, $NiCl_2$ and $CoCl_2$.

The demthylation (ether cleavage) of 4,5-dichloro-2-(4-chlorophenoxy)anisole can be carried out by methods which are known per se. Suitable acids for the reaction are proton acids, e.g. hydrohalic acids, especially hydrobromic acid, or Lewis acids, e.g. $BF_3$ and, in particular, $AlCl_3$. The reaction is carried out in an inert solvent. The reaction is preferably carried out in aqueous medium if a hydrohalic acid is used, and in an organic solvent if a Lewis acid is used. The demethylation is preferably carried out using $AlCl_3$ in benzene as solvent (cf. U.S. Pat. No. 3,629,477, Example 40, and Swiss patent specification No. 428 759).

Both steps of the process of the invention (chlorination and ether cleavage) can also be carried out consecutively without isolation of the intermediate, while if desired the solvent employed in the chlorination is removed by evaporation and replaced by another solvent. It is preferred, however, to isolate the intermediate.

As the chlorination proceeds exceedingly selectively, the desired 4,5-dichloro-2-(4-chlorophenoxy)anisole can be readily isolated from the reaction mixture without the necessity of the laborious separation of isomers and/or other chlorination products. The product normally precipitates direct from the solvent employed.

The starting 2-phenoxyanisole can be readily obtained e.g. by reaction of guaiacol (2-methoxyphenol) with bromobenzene by the method of H. E. Ungnade and E. F. Orwoll, Organic Synthesis, Vol. 3, 566, (1955).

The 4,5-dichloro-2-(4-chlorophenoxy)phenol obtainable by the process of the present invention is distinguished, as already mentioned, by good antimicrobial properties. It can therefore be used for protecting a wide variety of substrates from attack by bacteria and fungi (cf. U.S. Pat. Nos. 3,800,048, 3,629,477 and 3,904,696; Swiss patent specification 432 119).

The invention is illustrated by the following Examples, in which percentages are by weight unless otherwise stated.

EXAMPLE 1

With stirring, 115 g (1.62 moles) of chlorine are introduced at 20°–25° C. into a solution of 84.2 g (0.42 mole) of 2-phenoxyanisole in 500 ml of dimethyl formamide in the course of 70 minutes. The reaction vessel is cooled with ice during the introduction of chlorine. With stirring, the reaction mixture is poured into 3 liters of ice-water, whereupon the product crystallises out after about 5 minutes. The crystals are collected by filtration after a further 45 minutes, washed with 1 liter of water and recrystallised from 2.2 liters of methanol. The resultant 4,5-dichloro-2-(4-chlorophenoxy)anisole has a melting point of 105°–106° C.

Similar results are obtained by adding a catalytic amount (e.g. 0.1 to 5 g) of $FeCl_3$, $NiCl_2$ or $CoCl_2$ to the solution of 2-phenoxyanisole and repeating the above procedure.

EXAMPLE 2

With stirring, 11.5 g (0.16 mole) of chlorine are introduced at room temperature into a solution of 8 g (0.04 mole) of 2-phenoxyanisole in 75 ml of acetonitrile in the course of 20 minutes. Then the reaction mixture is stirred for 70 minutes at room temperature. The white suspension is cooled to 0° C. and the white crystals of 4,5-dichloro-2-(4-chlorophenoxy)anisole are collected by filtration and washed with two 10 ml portions of ice-cold acetonitrile. Further 4,5-dichloro-2-(4-chlorophenoxy)anisole can be isolated from the filtrate.

EXAMPLE 3

With stirring, 13 g (0.183 mole) of chlorine are introduced at room temperature into a solution of 8 g (0.01 mole) of 2-phenoxyanisole in 75 ml of methanol in the course of 1½ hours. The mixture is then stirred for 30 minutes at room temperature. After cooling to 0° C., the crystals are collected by filtration and recrystallised from methanol, affording 4,5-dichloro-2-(4-chlorophenoxy)anisole in the form of white crystals with a melting point of 105° C.

EXAMPLE 4

With stirring, 11.2 g of chlorine are introduced at room temperature into a solution of 8 g of 2-phenoxyanisole in 85 ml of chloroform in the course of 25 minutes. The mixture is then stirred for 30 minutes at room temperature. The solvent is removed by evaporation and the crystalline residue is recrystallised from methanol, affording 4,5-dichloro-2-(4-chlorophenoxy)anisole in the form of white crystals with a melting point of 105°–106° C.

EXAMPLE 5

With stirring, 11.2 g of chlorine are introduced at room temperature into a solution of 8 g of 2-phenoxyanisole in 85 ml of methylene chloride in the course of 20 minutes. The reaction mixture is subsequently stirred for 1 hour at room temperature. The solvent is removed by evaporation and the crystalline residue is recrystallised from methanol, affording 4,5-dichloro-2-(4-chlorophenoxy)anisole in the form of white crystals with a melting point of 105°–106° C.

Similar results are obtained if 0.5 g of triethylamine or 50 mg of iodine is added to the solution before the introduction of chlorine.

EXAMPLE 6

With stirring, 11.5 g of chlorine are introduced at room temperature into a solution of 8 g of 2-phenoxyanisole in 85 ml of 1,2-dichloroethane in the course of 20 minutes. The reaction mixture is then stirred for 30 minutes at room temperature. The solvent is removed by evaporation and the crystalline residue is recrystallised from methanol, affording 4,5-dichloro-2-(4-chlorophenoxy)anisole in the form of white crystals with a melting point of 105°–106° C.

EXAMPLE 7

With stirring, 11.5 g of chlorine are introduced at room temperature into a solution of 8 g of 2-phenoxyanisole and 0.3 g of iron(III)chloride in 85 ml of dimethyl formamide in the course of 35 minutes. The reaction mixture is then stirred for 30 minutes. After dilution with 200 ml of water, the precipitated crystals are collected by filtration and recrystallised from methanol, affording 4,5-dichloro-2-(4-chlorophenoxy)anisole in the form of white crystals with a melting point of 105° C.

EXAMPLE 8

With stirring, 11.5 g of chlorine are introduced at 25°–30° C. into a solution of 8 g of 2-phenoxyanisole in 50 ml of dimethylmethanephosphonate in the course of 30 minutes. The reaction mixture is then stirred for 1½ hours. The solvent is removed in vacuo (12 torr) at 90° C. and the residue is recrystallised from methanol, affording 4,5-dichloro-2-(4-chlorophenoxy)anisole in the form of white crystals with a melting point of 105°–106° C.

EXAMPLE 9

To a solution of 124 g (0.4 mole) of 4,5-dichloro-2-(4-chlorophenoxy)anisole (obtained according to any one of Examples 1 to 8) in 520 ml of benzene are added 157.4 g (1.1 moles) of aluminium chloride and the mixture is heated to reflux, with stirring, for 45 minutes. The suspension is cooled to room temperature, then poured, with stirring, onto a mixture of 970 g of ice and 970 ml of concentrated hydrochloric acid. The phases are separated in a separating funnel and the benzene phase is washed with four 250 ml portions of 5% sodium chloride solution. The benzene phase is then poured into 1 liter of 2N aqueous sodium hydroxide solution and 3 liters of water and the resultant suspension is heated, with stirring, to 60° C. The benzene phase is then separated and residual benzene is expelled from the aqueous phase by introducing steam. The aqueous solution is treated with animal charcoal and filtered. Then 400 of concentrated hydrochloric acid are added to the filtrate and the precipitated crystals are collected by filtration and washed with 1.5 liters of water.

Yield: 111.6 g of 4,5-dichloro-2-(4-chlorophenoxy)-phenol in the form of white crystals with a melting point of 92°–93.5° C.

What is claimed is:

1. A process for the manufacture of 4,5-dichloro-2-(4-chlorophenoxy)phenol, which comprises selectively chlorinating one molar equivalent of 2-phenoxyanisole at a temperature between −10° and +50° C., in a lower halogenated aliphatic hydrocarbon which contains at least one hydrogen atom, a lower aliphatic nitrile, dimethyl formamide, dimethylmethanephosphonate or methanol, with about 3 to 5 molar equivalents of chlorine, and demethylating the 4,5-dichloro-2-(4-chlorophenoxy)anisole obtained as intermediate with an acid.

2. A process for the manufacture of 4,5-dichloro-2-(4-chlorophenoxy)anisole, wherein 1 molar equivalent of 2-phenoxyanisole is selectively chlorinated with about 3 to 5 molar equivalents of chlorine at a temperature between −10° and 50° C. in a lower halogenated aliphatic hydrocarbon which contains at least one hydrogen atom, a lower aliphatic nitrile, dimethyl formamide, dimethylmethanephosphonate or methanol.

3. A process according to either of claims 1 or 2, wherein the chlorination is carried out in a chlorinated aliphatic hydrocarbon containing 1 to 4 carbon atoms and at least one hydrogen atom, an aliphatic nitrile containing 2 to 5 carbon atoms, dimethyl formamide, dimethylmethanephosphonate or methanol.

4. A process according to claim 3, wherein the solvent employed is dimethyl formamide, dimethylmethanephosphonate, methanol, acetonitrile, propionitrile, chloroform, methylene chloride, 1,2-dichloroethane or tetrachloroethane.

5. A process according to claim 4, wherein the solvent employed is dimethyl formamide, acetonitrile, methylene chloride or 1,2-dichloroethane.

6. A process according to claim 1 wherein the chlorination is carried out in the temperature range between 0° and 30° C.

7. A process according to claim 1, wherein the demethylation is carried out in an inert solvent with a proton acid, or a Lewis acid.

8. A process according to claim 7, wherein the acid employed is $AlCl_3$.

9. A process according to claim 7, wherein the acid employed is a hydrohalic acid.

10. A process according to claim 7, wherein the acid employed is $BF_3$.

* * * * *